United States Patent [19]

Kotsanis

[11] Patent Number: 4,459,978

[45] Date of Patent: Jul. 17, 1984

[54] MEDICAL RETRACTOR DEVICE

[75] Inventor: Constantine Kotsanis, River Grove, Ill.

[73] Assignee: Endoscopy Surgical Systems, Inc., White Haven, Pa.

[21] Appl. No.: 378,874

[22] Filed: May 17, 1982

[51] Int. Cl.³ ............................................. A61B 17/02
[52] U.S. Cl. ..................................... 128/20; 128/343
[58] Field of Search ............... 128/3, 4, 6, 20, 303.11, 128/345, 334 R, 335, 336, 341, 343

[56] References Cited

U.S. PATENT DOCUMENTS

| 1,244,751 | 10/1917 | McCleary | 128/345 |
| 1,344,227 | 6/1920 | Hauman | 128/334 R |
| 2,816,552 | 12/1957 | Hoffman | 128/341 |
| 2,940,451 | 6/1960 | Vogelfanger et al. | 128/334 R |

FOREIGN PATENT DOCUMENTS

| 514441 | 12/1930 | Fed. Rep. of Germany | 128/303.11 |
| 2054 | of 1884 | United Kingdom | 128/3 |

Primary Examiner—Edward M. Coven
Assistant Examiner—Max F. Hindenburg
Attorney, Agent, or Firm—John Kurucz

[57] ABSTRACT

An expandable fingers medical device which improves surgical speed and precision and enhances patient care and recovery by minimizing anesthesia time, trauma, infection and iatrogenic complications and increases viability of anastomosis. The medical device has fingers which expand and spread out in response to actuation of a control assembly. In the illustrative embodiment, the control assembly has a wrist mounting which holds the fingers and a wire rope for pulling the fingers against the cammed end of a tube. A threaded rod is secured to the distal end of the wire rope for threaded engagement with an internally threaded knob. When the knob is turned in one direction, the rod and wire rope are pulled causing the fingers to cam against the cammed end of the tube, thereby causing the fingers to spread apart. When the knob is turned in the opposite direction, the rod and wire rope are pushed causing the fingers to retract.

9 Claims, 4 Drawing Figures

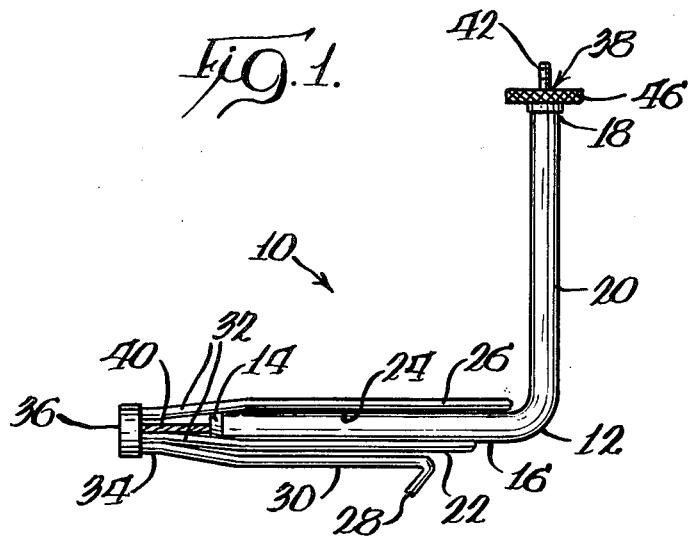
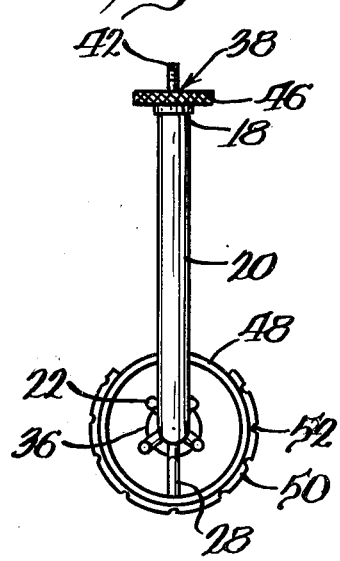
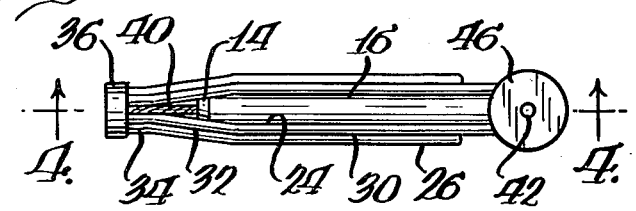
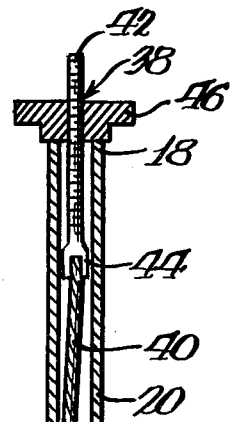
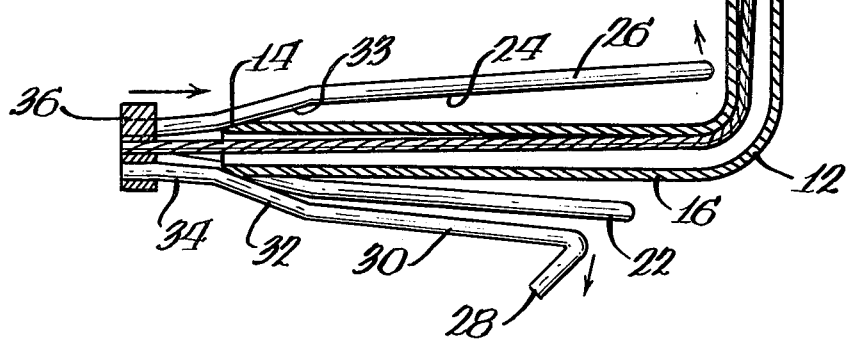

MEDICAL RETRACTOR DEVICE

DESCRIPTION

1. Technical Field

This invention relates to medical devices, and more particularly, to an intralumen retractor.

2. Background of the Invention

Patient care is of the utmost importance. Through simplification of existing techniques and providing a means to introduce new techniques, patient care can be greatly enhanced.

Over the years, a variety of retractors, and other related medical devices have been developed to enhance surgical techniques and provide for greater patient care. Typifying such retractors, catheters and other medical devices are those shown in U.S. Pat. Nos. 2,649,092, 3,397,699, 3,528,869, 3,692,029, 3,815,608, 4,202,332, 4,203,430, 4,144,884, 4,207,898 and 4,207,899. These retractors and other medical devices have met with varying degrees of success.

It is therefore desirable to provide an improved intralumen retractor which enhances surgical speed and precision during anastomosis of end to side procedures.

SUMMARY OF THE INVENTION

An expandable fingers medical device provides an intralumen retractor which improves surgical speed and precision during anastomosis of end to side procedures such as femoropopliteal bypass, fundoplasty and atrioventricular fistulas. The expandable fingers medical device permits a more precise approximation of a fishmouth during anastomotic procedures which leads to satisfactory patency of the anastomotic site and the desired graft.

The expandable fingers medical device improves patient care and recovery by minimizing anesthesia time, trauma infection and iotrogenic complication as well as increasing the viability of the anastomosis. Advantageously, the expandable fingers medical device is safe, efficient, reliable and easy to use.

To this end, the expandable fingers medical device has a set of fingers carried on a tubular frame. The fingers are provided with cam-engaging surfaces which face inwardly and generally towards each other as well as towards the cammed end of the tubular frame. One end of each of the fingers is connected to a wrist mounting. When the wrist mounting is pulled by a flexible strand, e.g., a wire rope, which extends through the cammed end of the tubular frame, the fingers are moved into camming engagement with the cammed end of the frame causing the fingers to expand and spread outwardly to engage and firmly grip the interior wall of the subject lumen. When the wrist mounting is pushed away from the cammed end of the frame by the flexible strand, the fingers retract.

As used throughout this application, the term "lumen" means a channel or cavity within a tubular organ of a patient. The lumen may be defined by a vessel, a tube or other organ of the human body.

In the illustrative embodiment, a threaded bifurcated clevis rod is clamped to the wire rope and a control knob is threadedly engaged to the clevis rod and seated upon the distal end of the tubular frame. When the knob is rotated in one direction, the wire rope is pulled. When the control knob is rotated in the opposite direction, the wire rope is pushed.

A more detailed explanation of the invention is provided in the following description and appended claims taken in conjunction with the accompanying drawings.

BRIEF DESCRIPTION OF THE DRAWINGS

FIG. 1 is a front view of a medical device in accordance with principles of the present invention;

FIG. 2 is an end view of the medical device after it has been positioned in a lumen;

FIG. 3 is a top plan view of the medical device; and

FIG. 4 is an enlarged cross-sectional view of the medical device taken substantially along the lines 4—4 of FIG. 3 with the fingers in a slightly expanded position.

DETAILED DESCRIPTION OF THE PREFERRED EMBODIMENT

Referring to the drawings, a mechanical, expandable fingers medical device 10 provides an intralumen retractor. Medical device 10 has a rigid tubular frame such as a rigid L-shaped tube 12. The horizontal front leg 16 of tube 12 has an inclined or beveled end 14 which provides a finger-expandable cam. The upright rear leg 20 of tube 12 has an upper distal end 18 which provides a shoulder upon which a knob 46 is rotatably seated.

A set of five expandable wire fingers 22 extend substantially over most of the length of the tube's front leg 16. Each of the fingers has an elongated distal phalanx, distalis phalanx or digitorummaus 30 integrally connected to a hookshaped fingertip 28, an intermediate middle phalanx, cam-engaging portion or phalanx media digitorummaus 32 which is inclined slightly inwardly of elongated distal phalanx 30, and a proximal phalanx or phalanx proximalis digitorummaus 34 which is tapered slightly inwardly and embedded or otherwise connected to a disc-like wrist mounting 36.

Fingers 22 have elongated inwardly facing portions or surfaces 24 which face towards each other as well as towards the front leg 16, and have outwardly facing portions 26 which face away from the front leg 16. The inwardly facing cam-engaging surfaces or cam followers 33 of the middle phalanxes 32 diverge outwardly and face generally towards each other as well as generally towards the cammed end 14 of tube 12. The hookshaped fingertips are reverse bent and curved outwardly of the inwardly facing portions 24 of fingers 22.

A control assembly is provided to pull the cam-engaging portion 32 of fingers 22 against the cammed end 14 of tube 12 in order to move fingers 22 from a retracted position to an expanded position. In the illustrative embodiment, control assembly 38 includes a wire rope 40 which is embedded or otherwise connected to the wrist mounting 36. Wire rope 40 extends through the tube's front leg 16 and partway through the tube's upright leg 20. A threaded rod or clevis 42 with a bifurcated lower end 44 securely clamps the distal end of wire rope 40 within the interior of the tube's upright leg 20. Threaded rod 42 extends out of the top end 18 of tube 12, and is in threaded engagement with a knurled, internally-threaded control knob or nut 46. Knob 46 is seated upon the top end 18 of tube 12.

In use, the expandable fingers medical device 10 is inserted with its fingers 22 in the retracted position into a lumen 48 (FIG. 2) of a patient. After the medical device 10 has been moved to the desired anatomical site, control knob is rotated clockwise to pull wire rope 40 and wrist mounting 36 towards the tube's cammed end 14 causing the cam-engaging surfaces 33 of fingers 22 to cammingly engage, abut against and ride upon the tube's cammed end so that the fingers expand and spread outwardly and away from the tube's front leg 16 to firmly engage the internal wall of the lumen and retain the medical device at said desired anatomical site. The amount of expansion of fingers 22 is controlled by the amount of rotation of knob 46.

In order to retract fingers 22, knob 46 is rotated in the opposite direction (counterclockwise) to push wrist mounting 36 away from the cammed end 14 of tube 12.

In the preferred embodiment, an auxiliary C-ring or hinged type ring 50 (FIG. 2) with suture guides in the form of equally spaced notches 52 is placed around the exterior wall of the lumen 48 prior to expansion of fingers 22. C-ring 50 clamps the expanded fingers against the lumen to enhance the holding ability of the fingers 22. Suture guides 52 provide equal spacing of sutures for a more precise approximation of the subject lumen.

C-ring 50 (FIG. 2) aids the surgeon during closure of the anastomosis and also helps avoid unnecessary intraoperative trauma and postoperative complications, such as bleeding through the suture line and necrosis of the anastomotic site, as well as increases the potential patency of the lumen.

Medical device 10 can be used in the cardiovascular system for endarterectomy, valve replacement, arterial bypass, venous bypass, A-V shunts, coronary bypass, cannulation, resection of aneurysms and traumatic repair of vessels. Medical device 10 can also be used in the gastrointestinal system for gastrectomy, small bowel resection, collectomy, ileostomy, collostomy, fistulectomy, esophangal repair and pancreatobiliary tree repair. Medical device 10 can further be used in the genito-urinary system for ureter repair, re-implantation, bladder repair, urethra repair, urostomy, kidney transplant, salpingoplasty, hysterectomy, vaginal repair and fistulectomy.

In some circumstances, it may be desirable to use a flexible tube rather than a rigid tube 12 so that the tube will bend and conform to the configuration of the subject lumen. Different sized fingers can also be used and the tube's cammed end can have an irregular contour or be divided into separate cam sections to engage and expand the fingers at different times, if desired by the surgeon.

Although an embodiment of the invention has been shown and described, it is to be understood that various modifications and substitutions, as well as rearrangement of parts, can be made by those skilled in the art without departing from the novel spirit and scope of the invention.

What is claimed is:

1. A medical device, comprising:
   tube means having a cammed end and a distal end;
   wrist mounting means axially spaced from said tube means;
   a plurality of fingers each having an unattached end and an attached end connected to said wrist mounting means, each of said fingers having a cam-engaging surface facing generally inwardly and towards said cammed end of said tube means; and
   pulling means extending through said tube means for pulling said inward cam-engaging surfaces of said fingers into camming engagement with said cammed end of said tube means to move said fingers from a retracted position to an expanded position to engage against the internal wall of a tubular organ and retain the medical device at a desired anatomical site.

2. A medical device in accordance with claim 1 wherein each of said fingers has a proximal phalanx and a distal phalanx and said cam-engaging surface is positioned intermediate and connected to said proximal phalanx and said distal phalanx.

3. A medical device in accordance with claim 2 wherein each of said fingers has a hooked end extending outwardly from said distal phalanx.

4. A medical device in accordance with claim 1 wherein said pulling means includes a wire rope.

5. A medical device in accordance with claim 4 wherein said wire rope is connected to said wrist mounting means.

6. A medical device in accordance with claim 4 wherein said pulling means includes a threaded rod clampingly engaging said wire rope and an internally threaded control knob seated upon said distal end of said tube means for threadedly engaging said threaded rod.

7. A medical device in accordance with claim 1 wherein said tube means is generally L-shaped.

8. A medical device in accordance with claim 1 further including a C-ring for clamping said fingers against said lumen when said fingers are in an expanded position.

9. A medical device in accordance with claim 8 wherein said C-ring defines a plurality of notches which provide a suturing guide.

* * * * *